(12) United States Patent
Miao et al.

(10) Patent No.: US 11,311,043 B2
(45) Date of Patent: Apr. 26, 2022

(54) PREPARATION OF GLUCAN-BASED SHELL-CORE STRUCTURE CARRIER MATERIAL AND ITS APPLICATION THEREOF

(71) Applicant: Jiangnan University, Wuxi (CN)

(72) Inventors: Ming Miao, Wuxi (CN); Bo Jiang, Wuxi (CN); Yang Qi, Wuxi (CN); Zhengyu Jin, Wuxi (CN); Chen Chen, Wuxi (CN); Tao Zhang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 272 days.

(21) Appl. No.: 16/368,429

(22) Filed: Mar. 28, 2019

(65) Prior Publication Data

US 2019/0239553 A1     Aug. 8, 2019

Related U.S. Application Data

(63) Continuation of application No. PCT/CN2018/075794, filed on Feb. 8, 2018.

(51) Int. Cl.

| | | |
|---|---|---|
| *C12P 19/18* | (2006.01) | |
| *A23P 10/30* | (2016.01) | |
| *C12P 19/04* | (2006.01) | |
| *A23L 33/105* | (2016.01) | |
| *A23L 33/12* | (2016.01) | |
| *A23L 33/125* | (2016.01) | |

(52) U.S. Cl.
CPC ............. *A23P 10/30* (2016.08); *A23L 33/105* (2016.08); *A23L 33/12* (2016.08); *A23L 33/125* (2016.08); *C12P 19/04* (2013.01); *C12P 19/18* (2013.01); *A23V 2002/00* (2013.01); *A23V 2200/224* (2013.01); *A23V 2200/30* (2013.01); *A23V 2250/1872* (2013.01); *A23V 2250/5118* (2013.01); *C12Y 204/01001* (2013.01)

(58) Field of Classification Search
CPC ........ A23V 2250/5118; A23V 2002/00; A23V 2200/30; A23V 2200/224; A23V 2250/1872; A23L 33/12; A23L 33/125; A23L 33/105; C12P 19/18; C12P 19/04; A23P 10/30; C12Y 204/01001
See application file for complete search history.

(56) References Cited

FOREIGN PATENT DOCUMENTS

| | | |
|---|---|---|
| CN | 1455818 A | 11/2003 |
| EP | 0710674 A2 | 5/1996 |
| EP | 0675137 B1 | 6/2001 |

*Primary Examiner* — Satyendra K Singh
(74) *Attorney, Agent, or Firm* — IPro, PLLC; Na Xu

(57) ABSTRACT

The present invention discloses a glucan-based shell-core structure carrier material and preparation and application thereof, and belongs to the technical field of modern food processing. Spherical hyperbranched water-soluble amylum grains are used as the raw material, and an enzymatic grafting and chain extending process is adopted for treatment to modify the surfaces of water-soluble glucan molecules into a firm shell structure with densely cumulated crystal structures, and form the glucan-based carrying material with the shell-core structure of which an inner core cavity has an amorphous state and an outer shell layer has a crystalline state. The adopted spherical hyperbranched water-soluble amylum grains have wide sources of raw materials and are not limited by producing areas and seasons; the preparation has simple and convenient steps, easy operation, controllable reaction conditions, relatively low cost and basically no pollution to the environment; and the prepared product can effectively protect, deliver and release functional nutritional components, can be applied to multiple fields of food, medicine, chemicals for daily use and the like, and has great market prospects and broad economic benefits.

9 Claims, 2 Drawing Sheets

PREPARATION OF GLUCAN-BASED SHELL-CORE STRUCTURE CARRIER MATERIAL AND ITS APPLICATION THEREOF

TECHNICAL FIELD

The disclosure herein relates to a glucan-based shell-core structure carrier material and preparation and application thereof, and belongs to the technical field of modern food processing.

BACKGROUND

With the development of social science and technology and economy, the transformation of lifestyles and the deterioration of the environment, the spectrum of diseases in China have changed. The number of chronic diseases such as diabetes, high blood pressure and obesity has increased dramatically, and the population of sub-health status has become larger and larger. At the same time, people's awareness of health care has become stronger and stronger, and the concept of medical care has changed from treatment after disease to preventive health care. People pay more and more attention to prevent chronic diseases through healthy lifestyle, dietary nutrition and other means.

Functional foods have become an important way to prevent or reduce the occurrence of chronic diseases in consumer diets due to their remarkable physiological functions. However, many natural active components have characteristics such as high melting point, poor water solubility, easy photolysis and easy oxidative decomposition, and are not easily digested and absorbed by the human body. Therefore, designing an effective active component delivery system to improve the utilization rate of biologically active substances is becoming the focus of research in the field. At present, Roche Pharmaceuticals, DSM, BASF and other major natural nutrient production suppliers abroad have developed microcapsules and emulsion protection technologies for natural nutrients and formed large-scale production and sales. Based on this, the present invention has conducted a detailed study on a processing method for improving the solubility and bioavailability of fat-soluble components.

Today, environmental protection and resource conservation have become the basic strategies for achieving sustainable development in all countries of the world. Under the situation of tight global resource supply and increasingly prominent environmental problems, the demand for low-carbon economy is growing stronger, and biological carrying materials with renewable resources as raw materials will be rapidly developed and widely used. Biological carrying materials converted from high-molecular materials as raw materials are used as international strategic emerging industries. At present, the application of protein biomacromolecules in the field of pharmacy is developing rapidly. For example, Yeonhee Yund et al. found oral target protein nanoparticle drug carriers. However, these drug carriers have relatively poor gastrointestinal stability; they are variable and are not easy to absorb, which affects their bioavailability. Among the carrying materials using starch-based raw materials, for example, Zhang Genyi, Yang Ying et al., in CN101293998, discloses a method for preparing a water-soluble nano-functional fatty acid complex carrier. However, the obtained carrying complex has a lower yield, a larger loss of raw materials, and a relatively complicated manufacturing process.

SUMMARY

For solving the above problems, the present invention provides a glucan-based shell-core structure carrier material capable of being embedded with a functional nutritional component and a processing method thereof. The glucan-based shell-core structure carrier material adopts soluble amylum grains, the amylum grains are modified by a biotechnology to form a special shell-core structure of which an inner core cavity has an amorphous state and an outer shell layer has a crystalline state, and in the process, nutritional factors are carried by a vine winding method. The glucan-based shell-core structure carrier material provided by the present invention can improve the biological stability, biological utilization effectiveness and slow-release effect of functional active components. The processing method provided by the present invention has the characteristics of simple production process, high yield, advanced technology, high safety, capability of protecting and regulating delivery and release of the functional nutritional component, and the like.

The first aim of the present invention is to provide a glucan-based shell-core structure carrier material capable of being embedded with a functional nutritional component, and the glucan-based shell-core structure carrier material is obtained by performing grafting and chain extending on glucosyl groups on the outer surfaces of spherical hyperbranched water-soluble starch particles by α-1,4 glycosidic bonds by using glycosyltransferase.

In one embodiment of the present invention, the molecular weight of the water-soluble starch particles is 107-108 g/mol, the proportion of α-1,6 glycosidic bonds is 7%-10%, and the average particle size is 30-100 nm.

In one embodiment of the present invention, the spherical hyperbranched water-soluble starch particles can be from natural plant spherical hyperbranched starch granules, oyster glycogen in animals, biotechnology-synthesized high-molecular spherical polysaccharides, and the like.

In one embodiment of the present invention, the spherical hyperbranched water-soluble starch particles are from sugary-type soluble corn glucan.

In one embodiment of the present invention, the glycosyltransferase can adopt glycogen phosphorylase, α-glucose phosphorylase and the like.

In one embodiment of the present invention, the embedded functional nutritional components comprise linoleic acid, linolenic acid, Q10 and the like.

In one embodiment of the present invention, a reaction system of grafting and chain extending also contains a functional component.

In one embodiment of the present invention, the glucan-based shell-core structure carrier material is prepared by preparing a solution from the water-soluble starch particles, then performing a reaction in a system containing donor molecules for providing glucose molecules and the glycosyltransferase, and performing enzyme deactivation, centrifugation, drying and precipitation after the reaction to obtain the glucan-based shell-core structure carrier material.

In one embodiment of the present invention, the mass ratio of the donor molecules for providing glucose molecules to the water-soluble starch particles is (1.5:1) to (5:1).

In one embodiment of the present invention, the donor molecule for providing glucose molecules is glucose-1-phosphate.

In one embodiment of the present invention, the glucose-1-phosphate can adopt a sodium salt or a potassium salt.

In one embodiment of the present invention, during preparation, the sweet-type soluble corn glucan is used as a main raw material, and grafting and chain extending are performed on the spherical hyperbranched corn glucan by using the glycosyltransferase to form a carrying material with a glucan-based shell-core structure of which an inner core cavity has an amorphous state and an outer shell layer has a crystalline state.

In one embodiment of the present invention, the preparation comprises the specific processing steps:

(1) dissolving water-soluble starch particles in a buffer solution to prepare a uniform solution with the mass concentration of 0.5-3.0%;

(2) according to the proportions of 1.5-5 g of glucose-1-phosphate and 10-180 U of glycosyltransferase per 1 g of water-soluble starch particles, adding the glucose-1-phosphate and the glycosyltransferase, performing uniform stirring, and performing a thermostatic reaction at the temperature of 35-40° C. and the pH value of 6.5-7.5 for 3-24 h; and (3) performing enzyme deactivation by heating and centrifugation treatment, and performing vacuum drying on the obtained precipitate to obtain the glucan-based shell-core structure carrier material.

In one embodiment of the present invention, the buffer solution is a Tris-HCl buffer solution, and optionally, the buffer solution is 50 mmol/L and 7.0 in pH value.

The second aim of the present invention is to provide a complex embedded with a functional component, and the complex is prepared by adding the functional component to a reaction system in the formation process of the glucan-based shell-core structure carrier material provided by the present invention.

In one embodiment of the present invention, the functional component can be a nutritional component, such as linoleic acid, linolenic acid, Q10 and the like.

The third aim of the present invention is to provide a biological carrying material containing the glucan-based shell-core structure carrier material provided by the present invention.

The fourth aim of the present invention is to provide application of the glucan-based shell-core structure carrier material in the aspect of carrying.

In one embodiment of the present invention, a carried substance is a medicine or a functional nutritional component.

The fifth aim of the present invention is to provide application of the glucan-based shell-core structure carrier material in the fields of food, medicine, chemicals for daily use and the like, including but not limited to functional factor targeted controlled release, nanoparticle embedding and the like.

Spherical hyperbranched water-soluble starch particles provided by the present invention are used as the raw material, and an enzymatic grafting and chain extending process is adopted for treatment to modify the surfaces of water-soluble glucan molecules into a firm shell structure with densely cumulated crystal structures, and form the glucan-based carrying material with the shell-core structure of which an inner core cavity has an amorphous state and an outer shell layer has a crystalline state, and the glucan-based shell-core structure carrier material has the following advantages:

(1) The spherical hyperbranched water-soluble starch particles adopted by the present invention can fully utilize resourceful cereal raw materials in China, have wide sources of raw materials and are not limited by producing areas and seasons, the raw materials have biodegradability and environmental friendliness, and especially natural corn polysaccharides have superior biological compatibility and are more applicable to the field of medicine.

(2) The present invention has simple and convenient steps, easy operation, controllable reaction conditions, relatively low cost and basically no pollution to the environment due to adoption of a clean and green production process.

(3) The product prepared by the present invention can effectively protect, deliver and release functional nutritional components, can be applied to multiple fields of food, medicine, chemicals for daily use and the like, such as functional factor targeted controlled release, nanoparticle embedding and the like, and has great market prospects and broad economic benefits.

DETAILED DESCRIPTION

To better realize the present invention, biological stability is characterized by determining the oxidation rate POV (peroxide value) by applying a potassium thiocyanate POV determining method. POV is calculated through the formula below:

$$POV\left(\frac{mequiv}{kg}\right) = \frac{(c - c0)}{(m \times 55.84 \times 1)},$$

c and $c_0$ are the mass of iron in a test sample and a blank sample; m is the mass of CLA; 2 is a conversion factor; and 55.84 is the relative atomic mass of iron. The degree of oxidation of pure nutritional factors serves as control, and the maximum values of the amount of peroxide (POV) in the control and the material are calculated and compared. POV is the amount of peroxide in a first stage product obtained after fat oxidation. Because it cannot be excluded that a small amount of peroxide continues to decompose into small molecular substances under an oxidizing environment, the stability is characterized by:

Stability≤(100−100 g CLA maximum value of the amount of peroxide generated by oxidation)/100*100%.

Cell experiment: Intestinal cell experiment is performed on a carrying complex. 100 μL of a carrying material-nutritional factor complex dissolved solution is added to a cell culture solution, 2 mM of a hydrogen peroxide solution is added for irritating cells for 2 h, and the cells are continued to be cultured for 4 h. Cell activity is detected by an MTT method.

Example 1

1 g of spherical hyperbranched water-soluble amylum grains (sweet-type soluble corn glucan) are weighted, and the amylum grains are dissolved in a Tris-HCl buffer solution (50 mmol/L, pH7.0) for preparing a uniform solution with the mass concentration of 0.5%. 1.5 g of glucose-1-phosphate and 40 U of glycosyltransferase is continually added, uniform stirring is performed, and a thermostatic reaction at the temperature of 40° C. and the pH value of 7.0 is performed for 12 h. Enzyme deactivation by heating and centrifugation treatment are performed, and vacuum drying is performed on the obtained precipitate to obtain the glucan-based shell-core structure carrier material.

Figure 1:
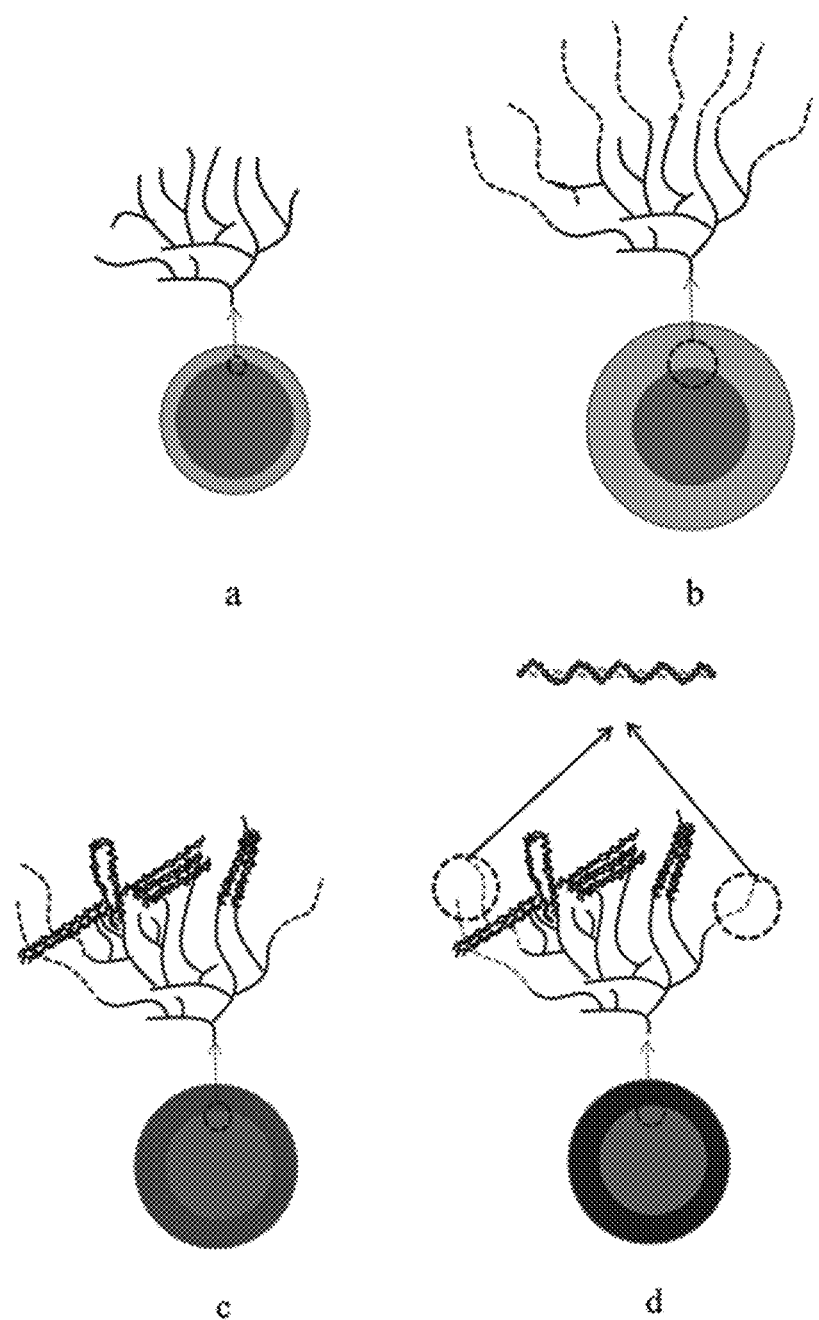
FIG. 1 is schematic diagrams of a carrying material with a shell-core structure and a complex of the carrying material with the shell-core structure and nutritional factors.

As shown in FIG. 1, a represents the spherical hyperbranched water-soluble amylum grains; b represents the early stage of grafting and chain extending when the amylum grains are modified by a biotechnology, i.e., glucosyl groups are sequentially connected to non-reducible terminals of the spherical starch granules by α-1,4 glycosidic bonds by the glycosyltransferase; c represents the later stage of grafting and chain extending after the amylum grains are modified by the biotechnology, i.e., linear chain structures formed by grafting are wound and crosslinked on the outer surfaces of the spherical amylum grains, double spiral structures are formed in partial positions, and further a shell-core structure of which an inner core cavity has an amorphous state and an outer shell layer has a crystalline state is formed by accumulation and gathering; d represents the complex of the carrying material and nutritional factors obtained by a vine winding method, i.e., due to interior hydrophobicity and exterior hydrophilicity, linear chain single spiral structures generated by grafting and chain extending can include the nutritional factors to form the complex of the carrying material and the nutritional factors by hydrophobic interaction.

Figure 2:
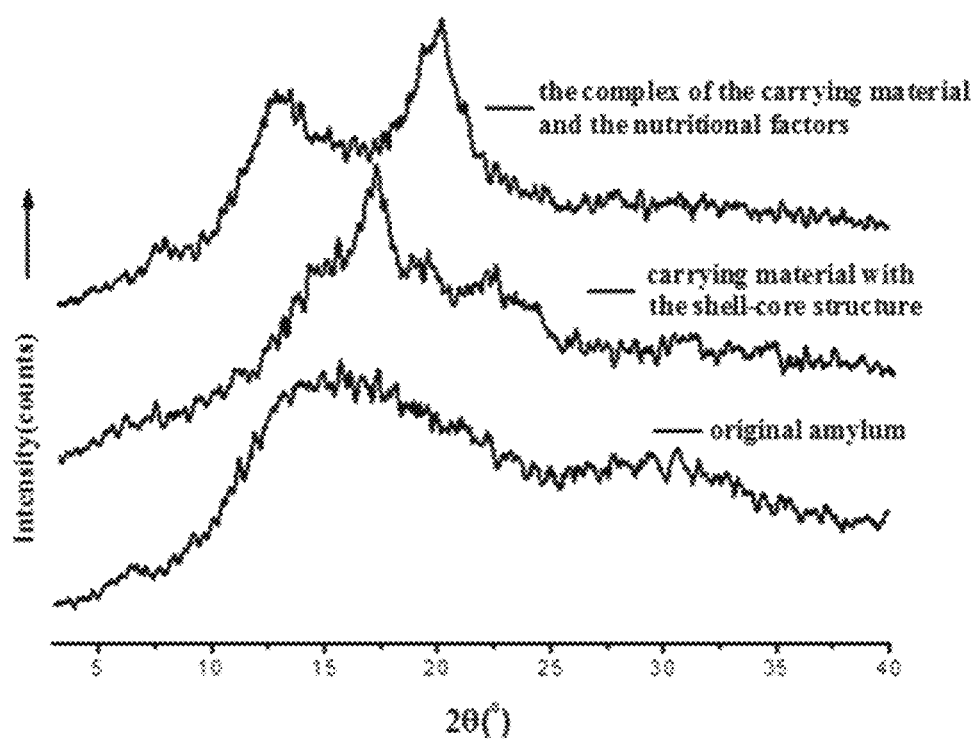
FIG. 2 is X-ray diffraction pattern results of original amylum grains and the carrying material with the shell-core structure.

FIG. 2 is X-ray diffraction pattern results of original amylum grains and the carrying material with the shell-core structure. The results show that an amorphous form is changed into a certain crystal structure.

TABLE 1

Properties of Carrying Material with Shell-core Structure

| Sample | Crystallinity (% ±3%) | Crystal size (nm) |
|---|---|---|
| Original amylum | 0 | 0 |
| Carrying material with shell-core structure | 23.54 | 5.084 |

Example 2

1 g of spherical hyperbranched water-soluble amylum grains (sweet-type soluble corn glucan) are weighted, and the amylum grains are dissolved in a Tris-HCl buffer solution (50 mmol/L, pH7.0) for preparing a uniform solution with the mass concentration of 1.0%. 2.5 g of glucose-1-phosphate and 60 U of glycosyltransferase are continually added, uniform stirring is performed, and a thermostatic reaction at the temperature of 40° C. and the pH value of 7.0 is performed for 18 h. Enzyme deactivation by heating and centrifugation treatment are performed, and vacuum drying is performed on the obtained precipitate to obtain the glucan-based shell-core structure carrier material.

Example 3

1 g of spherical hyperbranched water-soluble amylum grains (sweet-type soluble corn glucan) are weighted, and the amylum grains are dissolved in a Tris-HCl buffer solution (50 mmol/L, pH7.0) for preparing a uniform solution with the mass concentration of 1.5%. 5.0 g of glucose-1-phosphate and 100 U of glycosyltransferase are continually added, uniform stirring is performed, and a thermostatic reaction at the temperature of 40° C. and the pH value of 7.0 is performed for 24 h. Enzyme deactivation by heating and centrifugation treatment are performed, and vacuum drying is performed on the obtained precipitate to obtain the glucan-based shell-core structure carrier material.

Example 4: Application of Glucan-Based Shell-Core Structure Carrier Material

The glucan-based shell-core structure carrier material prepared in Examples 1-3 is applied to carrying of a functional active substance conjugated linoleic acid. A specific test method is as follows:

Nutritional factors are added during the grafting and chain extending reaction of amylum grains, i.e., 1 g of spherical hyperbranched amylum grains are dissolved in a buffer solution, 5.0 g of glucose-1-phosphate, 100 U of enzymes and 10 mg of nutritional factors conjugated linoleic acid dissolved in a small amount of ethanol are continually added, mixing and uniform stirring are performed, and a thermostatic reaction at the temperature of 40° C. and the pH value of 7.0 is performed for 24 h. Shell-core structure is formed after grafting and chain extending are finished, and because the structure contains single spiral cavities with hydrophobic effects, the structure car include nutrients to further form a complex. 15% sodium chloride solution can be added to accelerate the generation of products, and the carrying complex is obtained by performing centrifugation, washing with 50% alcohol and drying treatment.

TABLE 2

Conjugated Linoleic Acid-Carried Glucan-based Shell-core Structure Carrier Material

| | Biological stability | Uplift ratio of biological stability |
|---|---|---|
| Embodiment 1 | 91.4% | 33.2% |
| Embodiment 2 | 94.6% | 36.7% |
| Embodiment 3 | 97.3% | 39.1% |
| Control 1 | 58.2% | / |
| Control 2 | 88.7% | 30.5% |
| Control 3 | 89.5% | 31.3% | the control 1 is a blank control group, namely the nutritional factor conjugated linoleic acid.

In an implementation method of the control 2: amylose is dissolved in a dimethyl sulfoxide solution at 90° C., cooling is preformed to 30° C., the dimethyl sulfoxide solution containing the amylose is mixed with dimethyl sulfoxide containing conjugated linoleic acid with the same temperature, and single spiral-nutritional factor inclusion is finished; 20 times of deionized water and a 15% sodium chloride solution with the same temperature by volume are added to accelerate generation of products, and centrifugation, washing with 50% alcohol and drying treatment are performed to obtain a carrying material-nutritional factor complex.

In an implementation method of the control 3: 20 mg of maltose and 200 mg of glucose-1-phosphate are dissolved in 100 nM of a citric acid buffer solution (pH 7.0) containing 5 nM of adenosine monophosphate and 20 U of D-enzyme, 1 mg of phosphorylase is added, a reaction is performed at the temperature of 30° C. for 2 h, centrifugation is performed on reactant liquor, supernatant liquor is treated at 100° C. for 5 min, denaturase protein is removed by centrifugation, 50 U of glucoamylase is added to the supernatant liquor, and the precipitate is ring structure glucan; the obtained ring structure glucan is dissolved in a dimethyl sulfoxide solution at 90° C., cooling is performed to 30° C., the dimethyl sulfoxide solution containing the ring structure glucan is mixed with dimethyl sulfoxide containing conjugated linoleic acid with the same temperature, and single spiral-nutritional factor inclusion is finished; 20 times of deionized water and a 15% sodium chloride solution with the same temperature by volume are added to accelerate generation of products, and centrifugation, washing with 50% alcohol and drying treatment are performed to obtain the carrying material-nutritional factor complex.

Example 5: Application of Glucan-Based Shell-Core Structure Carrier Material

The glucan-based shell-core structure carrier material prepared in Example 3 is applied to carrying of a functional active substance coenzyme Q10.

A specific test method is as follows:

Nutritional factors are added during the grafting and chain extending reaction of amylum grains, i.e., 1 g of amylum grains are dissolved in a buffer solution, 10.0 g of glucose-1-phosphate, 100 U of enzyme and 10 mg of nutritional factors coenzyme Q10 dissolved in a small amount of ethanol are continually added, mixing and uniform stirring are performed, and a thermostatic reaction at the temperature of 40° C. and the pH value of 7.0 is performed for 24 h. A shell-core structure is formed after grafting and chain extending are finished, and because the structure contains single spiral cavities with hydrophobic effects, the structure can include nutrients to further form a complex. A 15% sodium chloride solution can be added to accelerate the generation of products, and the carrying complex is obtained by performing centrifugation, washing with 50% alcohol and drying treatment.

TABLE 3

Intestinal Cell Experiment

| Cell activity % | Hydrogen peroxide solution 44 ± 2.0 | |
|---|---|---|
| | Coenzyme Q10 (1 µg/ml) 92 ± 3.4 | Carrying material coenzyme Q10 complex (1 µg/ml) 59 ± 2.7 |
| | Coenzyme Q10 (10 µg/ml) 97 ± 2.6 | Carrying material coenzyme Q10 complex (10 µg/ml) 82 ± 3.1 |

Example 6: Optimized Research on Conditions in Material Preparation Process (1) Spherical hyperbranched water-soluble amylum grains in 1 g of sweet-type soluble corn glucan are dissolved in a Tris-HCl buffer solution (50 mmol/L, pH7.0) for preparing a uniform solution with the mass concentration of 5.0%, and other conditions referred to the example 3 are unchanged to prepare a carrier material.

(2) Refer to the example 3, the addition amount of the glucose-1-phosphate is changed from 1.5 g to 10 g, and other conditions are unchanged to prepare a carrier material.

(3) Refer to the example 3, the addition amount of the glycosyltransferase is changed from 40 U to 250 U, and other conditions are unchanged to prepare a carrier material.

By referring to the example 4 and respectively applying the carrier materials obtained by the above three methods to carrying of a functional active substance conjugated linoleic acid, it is discovered that the biological stability of the 3 kinds of carrying complexes is relatively low, and does not exceed 75%, wherein the carrier material in the method (3) has no obvious improvement as compared with the control 1 (blank load).

The specific embodiments described herein are merely illustration of the spirit of the present invention and some of the experiments. A person skilled in the art can make various modifications or complements to the specific embodiments described or replace them in a similar manner, without departing from the spirit of the present invention or beyond the scope of defined in the appended claims.

What is claimed is:

1. A nutritional factor-conjugated glucan-based shell-core structure complex comprising:
    a glucan-based shell-core structure comprising an inner core cavity having an amorphous state and an outer shell layer having a crystalline state,
    α-1,6 glycosidic bonds in an amount of 7% to 10%, and
    one or more conjugated nutritional factors included within the inner core cavity to form the nutritional factor-conjugated glucan-based shell-core structure complex,
    wherein the structure of the nutritional factor-conjugated glucan-based shell-core complex demonstrates increased X-ray diffraction intensity as compared to a glucan-based shell-core structure that comprises no nutritional factors,
    wherein the one or more nutritional factors comprises linoleic acid, linolenic acid, or coenzyme Q10,
    wherein percent biological stability of the one or more nutritional factors is at least 91.4%, where the percent biological stability is measured as [(100−maximum value of peroxide generated by oxidation of CLA)/100]×100%, and where CLA is conjugated linoleic acid, linolenic acid, or coenzyme Q10,
    wherein the maximum amount of peroxide generated by the CLA oxidation is equal to $(c-c0)/(m \times 55.84 \times 2)$, where: c and c0 are the mass of iron in a test sample and a blank sample, respectively, and m is mass of the CLA,
    wherein the nutritional factor-conjugated glucan-based shell-core structure complex is produced by a process of:
    (a) dissolving water-soluble spherical starch particles in a buffer solution, wherein the buffer solution has a mass concentration of the starch particles in the range of 0.5% to 3.0%;
    (b) adding the one or more nutritional factors, a glucose donor, and a glycosyltransferase to the dissolved spherical starch particles of step (a) under reaction conditions to attach glucose molecules to the outer surface of the spherical starch particles via α-1,4-glycosidic bonds, thereby forming the nutritional factor-conjugated glucan-based shell-core structure comprising an inner core cavity having an amorphous state and an outer shell layer having a crystalline state; and
    (c) after performing step (b), deactivating the glycosyltransferase.

2. The nutritional factor-conjugated glucan-based shell-core structure complex of claim 1, wherein the water-soluble spherical starch particles have a molecular weight of $10^7$ to $10^8$ g/mol, and wherein an average particle size of the water-soluble spherical starch particles is in the range of 30 nm to 100 nm.

3. The nutritional factor-conjugated glucan-based shell-core structure complex of claim 1, wherein the spherical starch particles are from one or more selected from the group consisting of natural plant spherical starch granules, oyster glycogen, and synthesized spherical polysaccharides.

4. The nutritional factor-conjugated glucan-based shell-core structure complex of claim 1, wherein the solution of the water-soluble spherical starch particles is prepared first, followed by the addition of the glucose donor and the glycosyltransferase to the buffer solution, and after performing the reaction, deactivating the glycosyltransferase, centrifuging the buffer solution, and then drying the buffer solution.

5. The nutritional factor-conjugated glucan-based shell-core structure complex of claim 4, wherein the mass ratio of the glucose donor to the water-soluble spherical starch particles is in the range of 1.5:1 to 5:1.

6. The nutritional factor-conjugated glucan-based shell-core structure complex of claim 4, wherein the glucose donor is glucose-1-phosphate, or a sodium or potassium salt thereof.

7. The nutritional factor-conjugated glucan-based shell-core structure complex of claim 1, wherein the glycosyltransferase comprises glycogen phosphorylase and α-glucose phosphorylase.

8. The nutritional factor-conjugated glucan-based shell-core structure complex of claim 1, wherein the spherical starch particles are from soluble corn glucan.

9. A nutritional factor-conjugated glucan-based shell-core structure complex comprising:
   a glucan-based shell-core structure comprising an inner core cavity having an amorphous state and an outer shell layer having a crystalline state,
   α-1,6 glycosidic bonds in an amount of 7% to 10%, and
   one or more conjugated nutritional factors included within the inner core cavity to form the nutritional factor-conjugated glucan-based shell-core complex, wherein the structure of the nutritional factor-conjugated glucan-based shell-core complex demonstrates increased X-ray diffraction intensity as compared to a glucan-based shell-core structure that comprises no nutritional factors,
   wherein the one or more nutritional factors comprises linoleic acid, linolenic acid, or coenzyme Q10,
   wherein percent biological stability of the one or more nutritional factors is at least 91.4%, where the percent biological stability is measured as [(100−maximum value of peroxide generated by oxidation of CLA)/100]×100%, and where CLA is conjugated linoleic acid, linolenic acid, or coenzyme Q10,
   wherein the maximum amount of peroxide generated by the CLA oxidation is equal to $(c-c_0)/(m \times 55.84 \times 2)$, where: $c$ and $c_0$ are the mass of iron in a test sample and a blank sample, respectively, and $m$ is mass of the CLA,
   wherein the nutritional factor-conjugated glucan-based shell-core structure complex is produced by a process of:
   (a) dissolving 1 g of water-soluble spherical starch particles into a buffer solution to yield a buffer solution with a final mass concentration of 0.5% to 3.0% of spherical starch particles;
   (b) adding the one or more nutritional factors, glucose-1-phosphate, and glycosyltransferase to the dissolved spherical starch particles obtained from step (a) in a proportion of 1.5 to 5 g of glucose-1-phosphate to 10 U to 180 U of the glycosyltransferase per 1 gram of the water-soluble spherical starch particles under reaction conditions that result in attachment of glucose molecules to the outer surface of the spherical starch particles via α-1,4-glycosidic bonds, thereby forming the nutritional factor-conjugated glucan-based shell-core structure comprising an amorphous inner core cavity and a crystalline outer shell layer;
   (c) stirring the spherical starch particles obtained from step (b);
   (d) incubating the dissolved spherical starch particles of step (c) at temperature of 35° C. to 40° C. and pH of 6.5 to 7.5 for a period of 3 hours to 24 hours;
   (e) after step (d), deactivating the glycosyltransferase by heating;
   (f) centrifuging the heat treated solution to obtain a precipitate; and
   (g) vacuum drying the precipitate to obtain the nutritional factor-conjugated glucan-based shell-core structure complex.

\* \* \* \* \*